United States Patent [19]

Cleary et al.

[11] Patent Number: 5,651,672

[45] Date of Patent: Jul. 29, 1997

[54] ORTHODONTIC FORCE MODULE

[75] Inventors: James D. Cleary, Glendora; Russell A. Jordan, Rancho Cucamonga, both of Calif.

[73] Assignee: Minnesota Mining and Manufacturing Company, St. Paul, Minn.

[21] Appl. No.: 438,608

[22] Filed: May 10, 1995

[51] Int. Cl.$^6$ ................................................ A61C 3/00
[52] U.S. Cl. ................................................ 433/19; 433/18
[58] Field of Search ................................. 433/7, 18, 19, 433/21, 22, 24

[56] References Cited

U.S. PATENT DOCUMENTS

| | | |
|---|---|---|
| 741,687 | 10/1903 | MacDowell . |
| 787,861 | 4/1905 | Shelp ............................ 433/18 X |
| 1,002,536 | 9/1911 | Montag ........................... 433/22 |
| 2,959,856 | 11/1960 | Gurin ............................ 32/14 |
| 3,121,953 | 2/1964 | Asher ............................ 32/14 |
| 3,137,941 | 6/1964 | Andrews ......................... 32/14 |
| 3,158,934 | 12/1964 | Waldman ........................ 32/14 |
| 3,238,619 | 3/1966 | Brunson et al. ................. 32/14 |
| 3,315,359 | 4/1967 | Moss ............................. 32/14 |
| 3,530,583 | 9/1970 | Klein et al. .................... 32/14 |
| 3,618,214 | 11/1971 | Armstrong ...................... 32/14 A |
| 3,690,003 | 9/1972 | Gerber .......................... 433/19 |
| 3,758,947 | 9/1973 | Kesling ......................... 42/14 A |
| 3,798,773 | 3/1974 | Northcutt ....................... 32/14 E |
| 3,803,715 | 4/1974 | Wallshein ....................... 32/14 A |
| 3,879,850 | 4/1975 | Wallshein ....................... 32/14 A |
| 3,913,228 | 10/1975 | Wallshein ....................... 32/14 A |
| 3,997,970 | 12/1976 | Hodgson ........................ 32/14 R |
| 4,038,753 | 8/1977 | Klein ............................ 32/14 E |
| 4,054,997 | 10/1977 | Wallshein ....................... 32/14 A |
| 4,224,021 | 9/1980 | Foxman .......................... 433/18 X |
| 4,340,363 | 7/1982 | Klein et al. .................... 433/18 |
| 4,439,149 | 3/1984 | Devincenzo ..................... 433/6 |
| 4,462,800 | 7/1984 | Jones ............................ 433/19 |
| 4,551,095 | 11/1985 | Mason ........................... 433/19 |
| 4,708,646 | 11/1987 | Jasper ........................... 433/19 |
| 4,815,972 | 3/1989 | Howe ............................ 433/18 X |
| 4,849,032 | 7/1989 | Kawaguchi ..................... 148/11.5 R |
| 4,950,158 | 8/1990 | Barngrover et al. ............ 433/11 |
| 5,044,946 | 9/1991 | Cleary .......................... 433/18 |
| 5,074,874 | 12/1991 | Sterrett et al. ................. 433/19 X |
| 5,120,218 | 6/1992 | Hanson .......................... 433/19 |
| 5,317,074 | 5/1994 | Hammar et al. ................ 528/44 |
| 5,352,116 | 10/1994 | West ............................. 433/19 |
| 5,435,721 | 7/1995 | Vogt .............................. 433/19 |

FOREIGN PATENT DOCUMENTS 44 05 086  2/1994  Germany .

OTHER PUBLICATIONS

Search Report for PCT/US96/01135.
Brochure for Force A™ Rotation Wedge, "A"–Company, Inc., 1986.

*Primary Examiner*—Nicholas D. Lucchesi
*Attorney, Agent, or Firm*—Gary L. Griswold; Walter N. Kirn; James D. Christoff

[57] ABSTRACT

A force module useful in moving individual malpositioned teeth or entire dental arches during orthodontic therapy includes an elongated body made of an elastomeric material, with couplings at each end of the body for connection to selected orthodontic appliances. The couplings are preferably spaced inwardly from opposite ends of the body to reduce bending stresses, and optionally an enlarged head of the body is provided to retain each coupling in place. In certain embodiments, the body has an enlarged middle section to reduce likelihood of fracture. A resilient core made of a metallic material is optionally received in the body to enhance the stiffness of the force module.

36 Claims, 2 Drawing Sheets

ORTHODONTIC FORCE MODULE

BACKGROUND OF THE INVENTION

1. Field of the Invention

This invention relates to an intra-oral force module used in orthodontic treatment.

2. Description of the Related Art

Orthodontic treatment involves movement of malpositioned teeth to orthodontically correct positions. During treatment, tiny orthodontic appliances known as brackets are connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to molar teeth.

Various types of elastomeric devices, also known as force modules, are commonly used in orthodontic treatment. The resilient force of such modules in tension or compression is typically used to move a tooth or an orthodontic appliance relative to other teeth or orthodontic appliances. As one example, tiny O-ring devices are used as ligatures to secure the archwire in slots of the brackets. As another example, elongated devices, including chain-like modules having a number of interconnected O-ring portions, are sometimes stretched between selected brackets in order to move certain teeth relative to other teeth. Other devices are especially adapted to separate adjacent teeth or to rotate a tooth about its long axis.

Examples of known elastomeric devices are found in U.S. Pat. Nos. 3,530,583, 3,758,947, 4,038,753, 4,950,158 and 5,044,946. U.S. Pat. No. 5,317,074 describes improved elastomeric orthodontic force modules that are made of a material resistant to staining when exposed to foods or beverages such as mustard, tea and coffee.

The orthodontic treatment of some patients includes correction of the alignment of the upper dental arch with the lower dental arch. For example, certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

Orthodontic treatment of Class II and Class III malocclusions are commonly corrected by movement of the upper dental arch as single unit relative to movement of the lower dental arch as a single unit. To this end, pressure is often applied to each dental arch as a unit by applying pressure to the brackets, archwires or attachments connected to the brackets or archwires. In this manner, the Class II or Class III malocclusion can be corrected at the same time that the archwires and brackets are used to move individual teeth to desired positions.

Orthodontic force modules made of an elastomeric material have been used in the past to treat a Class II malocclusion by connecting a pair of such force modules to both arches on opposite sides of the oral cavity. In such instances, the force module may be used in tension to pull the jaws together in a direction along reference lines that extend between the points of attachment of each force module. Such force modules may be an O-ring or a chain-type module made of a number of integrally connected O-rings.

Conventional elastomeric force modules used in treatment of a Class II or Class III malocclusion are often removable by the patient for replacement when necessary and for cleaning of the teeth. Unfortunately, neglect of the patient to reinstall the force modules seriously retards the progress of treatment. Poor cooperation from the patient can defeat timely achievement of the goals of an otherwise well-planned treatment program, resulting in an additional expenditure of time for both the patient and the orthodontist. Patient cooperation is often a problem with adolescent patients.

A number of devices that are fixed in place in the oral cavity during orthodontic treatment have been proposed in the past to overcome the problems of patient cooperation associated with removable force modules. For example, U.S. Pat. Nos. 3,798,773, 4,462,800 and 4,551,095 disclose a telescoping tube assembly that urges the jaws toward positions of improved alignment. The assemblies are fixed to other orthodontic appliances by the orthodontist, and thus problems of patient non-compliance are avoided. The device shown in U.S. Pat. No. 3,798,773 includes an internal coil compression spring to exert force on the dental arches as the mouth is closed.

A coiled wire spring device used in tension for applying corrective forces between the dental arches is shown in U.S. Pat. No. 3,618,214 and includes, in one embodiment, a pair of fasteners such as eyelets secured to opposite ends of the coiled wire spring. A protective sheath is disposed around the spring. The spring produces a restoring force upon elongation that urges the jaws toward an improved alignment.

Other orthodontic devices for correcting Class II and Class III malocclusions are described in U.S. Pat. Nos. 4,708,646 and 5,352,116. Such patents describe flexible members with swivel end attachments for connection to the upper and lower jaws of a patient. The length of the members is selected such that the member is curved in an arc when the patient's jaws are closed. The inherent bias of the members toward a normally straight orientation provides a force that pushes one jaw forwardly or rearwardly relative to the other jaw.

The commercial embodiments of the devices described in U.S. Pat. Nos. 4,708,646 and 5,352,116 include internal coil springs that are surrounded by a plastic sheath. It has been observed in some instances that the coil spring may break during use after a period of time. Unfortunately, the plastic sheath often hides the broken portion of the spring, such that it is difficult to confirm that the device is working as intended.

There is a need in the art for an improved orthodontic force module that can be fixed in place by the orthodontist and can be used, among other things, for correcting Class II or Class III malocclusions. Preferably, such a force module would be relatively easy to manufacture, and yet provide reliable corrective force as desired by the orthodontist over the expected lifetime of its use.

SUMMARY OF THE INVENTION

The present invention is directed in one embodiment to an orthodontic force module that comprises a body having a longitudinal axis and made of an elastomeric material. The body has a first end section with a first, outermost end and a second end section with a second, outermost end. A first coupling is connected to the first end section for connecting the first end section to a selected orthodontic appliance in the oral cavity. The first coupling has an arm portion that extends at an obtuse angle relative to the longitudinal axis along a reference axis that intersects the body at a location spaced inwardly from the first end.

Another embodiment of the invention concerns an orthodontic force module that comprises a body having a longitudinal axis. The body has a first end section and a second end section. A first coupling is connected to the first end section and a second coupling is connected to the second end section for connecting the first end section and the second end section respectively to selected orthodontic appliances in the oral cavity. The body has a middle section located between the first end section and the second end section, and the middle section has a certain cross-sectional area in reference planes perpendicular to the longitudinal axis. The first end section and the second end section each have a cross-sectional area in reference planes perpendicular to the longitudinal axis that is less than the certain cross-sectional area.

Another aspect of the invention relates to an orthodontic force module that comprises a body having a longitudinal axis and made of an elastomeric material. The body has a first end section and a second end section. A first coupling is connected to the first end section and a second coupling is connected to the second end section for connecting the first end section and the second end section respectively to selected orthodontic appliances in the oral cavity. A resilient core is received at least partially within the body. The core has an elongated, substantially straight configuration extending in a direction substantially parallel to the longitudinal axis of the body. The core is made of a metallic material for enhancing the stiffness of the force module.

The present invention is also directed toward an orthodontic force module that comprises a body having a longitudinal axis and made of an elastomeric material. The body has a first end section with a first, outermost end and a second end section with a second, outermost end. A first coupling is connected to the first end section for connecting the first end section to a selected orthodontic appliance in the oral cavity. The first coupling has a through passageway. The body extends through the through passageway and has an enlarged head presenting the first end. The enlarged head is located outwardly of the first coupling for retaining the first coupling in connection with the first end section.

Further details of these and other aspects of the invention are set out in the detailed description that follows as well as in the accompanying drawings.

DETAILED DESCRIPTION OF THE PREFERRED EMBODIMENTS

Figure 1:
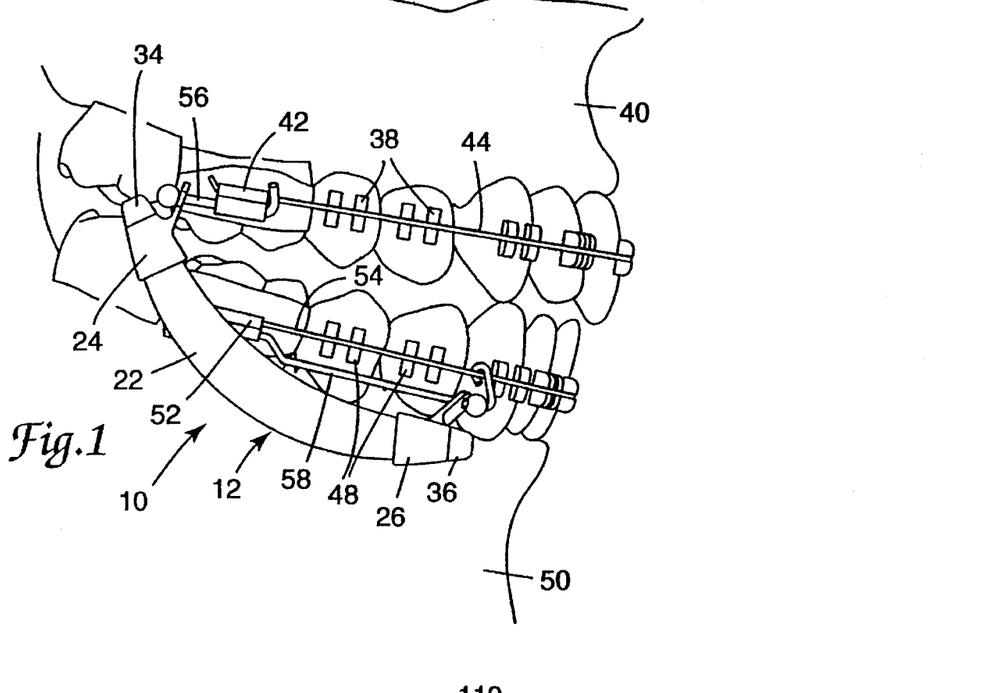
FIG. 1 is a side elevational view showing an orthodontic force module constructed in accordance with one embodiment of the present invention and installed in the oral cavity of a patient to show one example of use.
Figure 2:
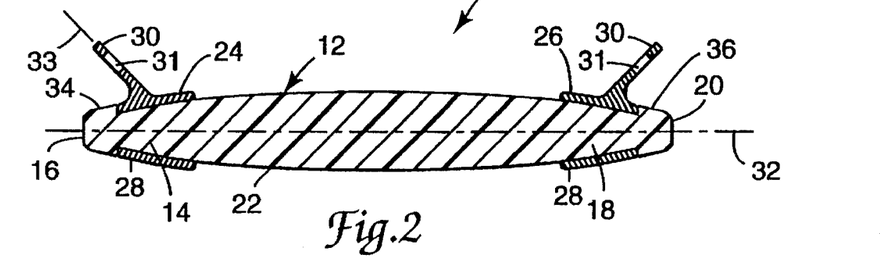
FIG. 2 is an enlarged side cross-sectional view of the force module alone that is illustrated in FIG. 1.
Figure 3:
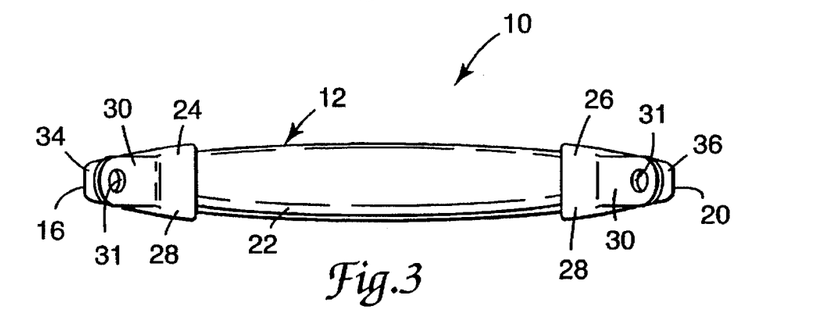
FIG. 3 is a plan view of the force module depicted in FIG. 2.

An orthodontic force module constructed in accordance with one embodiment of the invention is broadly designated by the numeral 10 in FIGS. 1–3. The force module 10 is illustrated in an exemplary use in the oral cavity of a patient in FIG. 1, and is shown alone in FIGS. 2 and 3.

Turning initially to FIGS. 2 and 3, the force module 10 includes an elongated body 12 that is made of an elastomeric material. The body 12 has a first end section 14 with a first, outermost end 16 and a second end section 18 with a second, outermost end 20. A middle section 22 is located between the first end section 14 and the second end section 18.

A first coupling 24 is fixed to the first end section 14 for connecting the first end section 14 to a selected orthodontic appliance in the oral cavity. The force module 10 also includes a second coupling 26 that is fixed to the second end section 18 of the body 12 for connecting the second end section 18 to another selected orthodontic appliance in the oral cavity. The first and second couplings 24, 26 are essentially identical. Each coupling 24, 26 has a sleeve portion 28 somewhat similar in shape to a hollow, truncated cone, and a generally flat, blade-like arm portion 30 that is integrally connected to the respective sleeve portion 28. Each arm portion has a circular hole 31.

As illustrated in FIG. 2, the body 12 has a central longitudinal axis designated 32. Each arm portion 30 extends along a reference axis (such as axis 33) that is oriented at an obtuse angle relative to the longitudinal axis 32. The obtuse angle is preferably 135°. The reference axis intersects the body 12 at a location spaced inwardly from the respective, adjacent end 16, 20.

Each coupling 24, 26 includes a through passageway. The first end section 14 of the body 12 extends through the through passageway of the first coupling 24 and terminates in a first enlarged, outer head 34 that presents the first end 16. Similarly, the second end section 18 of the body 12 extends through the through passageway of the second coupling 26 and terminates in a second enlarged, outer head 36 that presents the second end 20. Each head 34, 36 has a diameter in reference planes perpendicular to the longitudinal axis 32 that is larger than the diameter of the through passageway of the outer end of the adjacent coupling 24, 26. The heads 34, 36 each present a shoulder that retains the couplings 24, 26 in connection with the adjacent end sections 14, 18 respectively.

The portion of the body 12 that is between the heads 34, 36 has a generally ellipsoid, or football-like configuration. The middle section 22 has a cross-sectional area in reference planes perpendicular to the longitudinal axis 32 that is greater than the cross-sectional area of the end sections 14, 18 in reference planes perpendicular to the longitudinal axis 32. Moreover, the tapered configuration of the body 12 in portions of the end sections 14, 18 within the couplings 24, 26 respectively matches the configuration of the inner tapered wall defining the through passageways of the couplings 24, 26.

In the embodiment shown in FIGS. 1-3, each of the couplings 24, 26 is rotatably connected to the body 12, such that either coupling may be moved in an arc about the longitudinal axis 32 of the body 12 when desired. However, it is also possible to non-rotatably fix the couplings 24, 26 to the body 12 by the use of adhesive, interlocking tabs and grooves or other means so that the couplings 24, 26 cannot be rotated in an arc about the longitudinal axis 32. In instances where the couplings 24, 26 are non-rotatably fixed to the body 12, it is preferred that the arm portions 30 extend in rotative directions other than that shown in FIGS. 2 and 3; for example, the arm portion 30 of the first coupling 24 may be positioned 90 degrees about an arc extending in a reference plane perpendicular to the longitudinal axis 32 relative to the direction of extension of the arm portion 30 of the second coupling 26. As another option, one of the couplings 24, 26 may be rotatable relative to the body 12, while the other coupling 24, 26 is fixed relative to the body 12.

The elastomeric material of the body 12 is a natural or synthetic thermoset or thermoplastic polymer which at room temperature can be repeatedly bent and/or stretched and which, after removal of the tensile or bending forces, will quickly and forcibly return to its original length and straight configuration. As an example, the elastomeric material has a flexural modulus of 2300 p.s.i. (15.9 MPa) and a Shore A hardness in the range of 80 to 85. Preferably, the material can be stretched without breakage to at least 150% elongation (i.e., to a length that is one and one-half times its original length), and yet will quickly and forcibly return to approximately its original length after removal of the tensile force.

Exemplary elastomeric materials include urethanes (such as TECOFLEX brand urethane, no. EG85A, from Themedics, Inc.). Other suitable materials include elastomers that are sufficiently free of hydrocarbon-based polyether segments and hydrocarbon-based polyester segments to provide resistance to staining by common foods such as mustard, tea and coffee. The stain-resistant materials preferably have per 2 mm thickness a Hunter color difference when using a 2.5 cm illuminated opening of (a) less than 40 when compared to a Hunter white standard tile and (b) less than 33 after immersion in mustard solution for 30 minutes when compared to the material before immersion in mustard solution.

A first class of stain resistant elastomeric materials include thermoplastic rubber polymers such as those commercially available under the trademark KRATON from Shell Chemical Company. The elastomers are di-block or tri-block copolymers having a rubbery phase and a glassy phase. A second class of stain resistant materials include polyurethanes, polyureas and polyurethanes/ureas. These materials can be thermoplastic materials or crosslinked by heat or actinic radiation to provide set materials. A third class of stain resistant materials include silicones, which are preferably selected from (a) crosslinked silicone elastomers, (b) α-methyl styrene-silicone-α-methyl styrene block copolymers of the type ABA, ABAB or (AB) in a star (where "A" is a thermoplastic block and "B" is the elastomeric block), and (c) silicone polycarbonate block copolymers of the type ABAB.

A fourth class of stain resistant materials include α-olefin thermoplastics such as ethylene propylene dimer (EPDM) rubbers and ethylene propylene monomer (EPM) rubbers. These materials preferably contain from 30 to 100 weight percent of EPDM or EPM rubbers that are preferably non-oil-extended. A fifth class of stain resistant materials includes fluoroelastomers including three basic types, namely fluorocarbon, fluorosilicone and fluoroalkoxyphosphazene. Further description and examples of these five classes of stain-resistant elastomeric materials are set out in U.S. Pat. No. 5,317,074, the disclosure of which is expressly incorporated by reference herein.

The couplings 24, 26 may be cast or metal injection molded of a stainless steel alloy. Alternatively, the couplings 24, 26 are molded from a high strength thermoplastic such as VECTRA brand liquid crystal polymer, from Hoechst Celanese.

FIG. 1 represents one example of use of the force module 10 in the oral cavity of a patient. As shown, a set of bracket appliances 38 is attached to certain teeth of an upper jaw 40 of the patient while a buccal tube appliance 42 is connected to the right first molar of the upper jaw 40. An orthodontic archwire 44 extends through slots in the bracket appliances 38 and also passes through a channel of the buccal tube appliance 42.

A set of bracket appliances 48 is connected to teeth of the patient's lower jaw 50, and a buccal tube appliance 52 is fixed to the right first molar of the lower jaw 50. An archwire 54 extends through slots of the bracket appliances 48 and also extends through a channel of the buccal tube appliance 52.

The first end section 14 of the force module 10 is connected to the patient's upper jaw 40 by a pin 56 that extends through the hole 31 of the first coupling 24. The pin 56 has an enlarged ball head that serves to retain the first coupling 24 in connection with the buccal tube appliance 42. A stem of the pin 56 extends through an auxiliary passage in the buccal tube appliance 42 and is bent to securely retain the pin 56 in place.

The second end section 18 of the body 12 is connected to the bracket appliances 48 and the buccal tube appliance 52 of the patient's lower jaw 50 by means of an auxiliary wire 58 that extends through the hole 31 of the second coupling 26. A ball stop is fixed to the auxiliary wire 58 and contacts the arm portion 30 of the second coupling 26. A distal portion of the auxiliary wire 58 extends through a passage in the buccal tube appliance 52, while a mesial portion of the auxiliary wire 58 is bent and connected to the archwire 54 at a location between the patient's first bicuspid tooth and the cuspid tooth on the right side of the patient's lower jaw 50. Of course, many other orientations and positions of the force module 10 are also possible. Moreover, other means for attaching the force module 10 to the dental arches are also possible.

Typically, a second force module (not shown) that is similar to the force module 10 will be installed in a similar manner and orientation on the left side of the patient's dental arches, such that both force modules act in concert to correct the Class II malocclusion. The length of the force module 10 is selected so that the body 12 is bent in a curve as illustrated in FIG. 1 when the jaws 40, 50 are closed and an improper Class II malocclusion exists. However, the flexible and resilient body 12 has a memory that urges the body 12 toward a straight configuration. The inherent memory of the body 12 when bent as shown in FIG. 1 will cause a light force to be applied against the ball stops of the pin 56 and the auxiliary wire 58 when the jaws 40, 50 are closed, such that the upper jaw 40 is urged in a rearwardly direction while the lower jaw 50 is urged in a forwardly direction.

The proper length of the force module 10 is selected by measuring the distance between the ball stops of the pin 56 and the auxiliary wire 58 when the jaws 40, 50 are closed, and then choosing a force module wherein the distance between the holes 31 when the force module is in its normally straight, unbent configuration is approximately 30% greater than such measured distance. Consequently, when the force module is installed, its inherent tendency to assume a straight configuration provides a gentle yet effective force when the jaws 40, 50 are closed to correct the Class II malocclusion.

The ellipsoid shape of the body 12 is an advantage, in that the middle section 22 is greater in area than the area of the end sections 14, 18 when calculated in reference planes perpendicular to the longitudinal axis 32. The enlarged area of the middle section 22 helps the body 12 resist fracture that might otherwise occur after repeated cycling between a bent and straight configuration as the jaws 40, 50 are opened and closed. For example, if a force module having an elastomeric body of a cylindrical configuration was instead used, such a body may tend to eventually fracture in its middle section where stresses could tend to concentrate during bending. The rounded outer surface of the body 12 is also advantageous in that the lack of edges or corners helps avoid patient discomfort if the body 12 impinges against the patient's tissues.

Furthermore, the direction of extension of the arm portions 30 (as indicated by reference line 33) intersects the body 12 of the force module 10 at a location spaced inwardly from the adjacent ends 16 or 20. As a consequence, there is less curvature and therefore less stress of the body 12 when the jaws 40, 50 are closed in comparison to a force module wherein a similar reference line intersects the adjacent ends of the body. Such construction helps insure that the force module 10 will not fracture during its intended period of use and after repeated cycling between a bent configuration and a straight configuration.

Advantageously, the force module 10 is also extensible in use. For example, if the patient opens the jaws 40, 50 to such an extent that the force module 10 is straight and the arm portions 30 cannot further slide toward each other along the pin 56 and the auxiliary wire 58, the flexibility of the body 12 enables the latter to elongate. As a result, the opening motion of the jaws 40, 50 is dampened as the body 12 is stretched, and the opening movement is not suddenly halted as might occur, for example, if the force module was non-extendible. The dampening effect provides feedback to the user so that further opening movement of the jaws 40, 50 can be interrupted in sufficient time before the module 10 damages or pulls the pins or auxiliary wires away from their intended locations.

When the force module 10 is initially placed in the oral cavity by the orthodontist, the couplings 24, 26 are swiveled as needed about the longitudinal axis 32 such that the holes 31 are in a proper position to receive the pin 56 and the auxiliary wire 58. By swiveling the couplings 24, 26, the force module 10 can be used either on the fight side or on the left side of the dental arches. Advantageously, the overall length of the force module 10 does not increase or decrease as the couplings 24, 26 are rotated about the longitudinal axis 32 relative to the body 12, so that the force provided by the body 12 in use remains predictable with precision.

Figure 4:
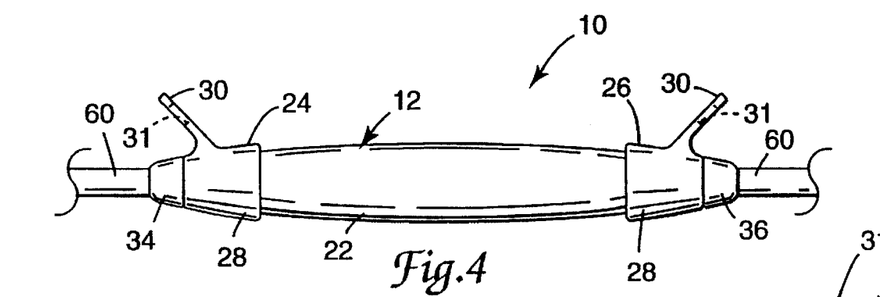
FIG. 4 is a side elevational view of the force module shown in FIGS. 1-3 as it appears during an intermediate step of manufacture according to one method of manufacturing the invention.
Figure 5:
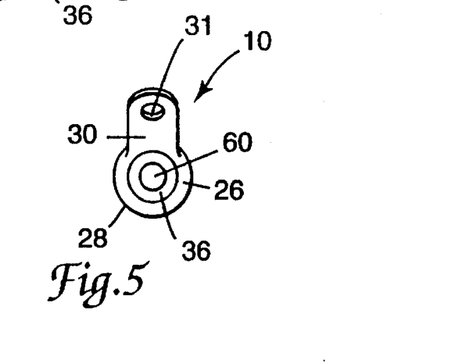
FIG. 5 is an end elevational view of the force module shown in FIG. 4.

FIGS. 4 and 5 illustrate the force module 10 during an intermediate step of one method of manufacture. As shown, the body 12 is initially provided with stem portions 60 that are integrally connected to the heads 34, 36 when the body 12 is molded (such as by injection molding). During assembly of the body 12 to the couplings 24, 26, the stem portions 60 are passed through the passageways of the respective couplings 24, 26 and then pulled away from each other. As the body 12 elongates, the enlarged heads 34, 36 are compressed and simultaneously forced through the passageways of the couplings 24, 26 until the heads 34, 36 are located outwardly of the couplings 24, 26. Next, tensile stress on the stem portions 60 is relieved, and the heads 34, 36 expand to retain the couplings 24, 26 on the body 12. Finally, the stem portions 60 are removed such as by a cutting operation.

Figure 6:
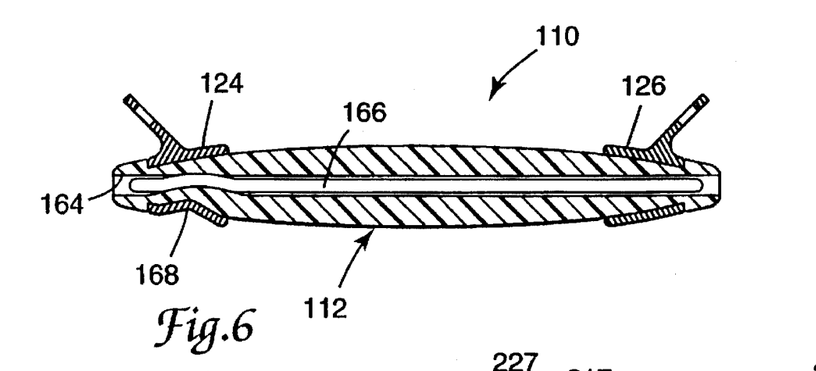
FIG. 6 is a side cross-sectional view of an orthodontic force module constructed in accordance with another embodiment of the invention.

Another embodiment of the invention is shown in FIG. 6, wherein a force module 110 includes an elastomeric body 112, a first coupling 124 and a second coupling 126. The body 112 and the couplings 124, 126 are essentially identical to the body 12 and the couplings 24, 26 described in connections with FIGS. 1–5 with the exception of the features described below and hence a detailed description of the identical features each item need not be repeated.

However, the body 112 includes a cylindrical through channel 164 extending from one end of the body 112 to the other along the central longitudinal axis of the body 112. A resilient core 166 is received within the channel 164 and preferably extends just beyond the outer end of each coupling 124, 126. The core 166 has an overall non-helical, substantially straight configuration and is made of a metallic material for enhancing the stiffness of the force module 110. The core 166 preferably has a greater stiffness than the stiffness of the elastomeric material comprising the body 112.

Preferably, the core is made of stainless steel or a shape memory type of alloy that exhibits super elasticity. Examples of suitable shape memory alloys include nitinol or similar alloys with substitutions to replace small amounts of either nickel or titanium. Other material that exhibit shape memory characteristics such as aluminum or bronze may also be used.

The core 166 may be made of a single strand, or of multiple strands that are braided or twisted together. Suitable cores may be made from straight lengths of wire used to make orthodontic archwires (such as Nitinol XL, Nitinol SE, Unitek Braided, Unitek Coaxial, Unitek Twist, Hi-T II Twist Flex or Flexiloy; all from 3M Unitek).

The first coupling 124 is crimped at the location designated 168 in FIG. 6 during a crimping operation. The crimping operation also compresses the portion of the body 112 within the first coupling 124 and crimps a first end portion of the core 166 as shown. The crimps serve to retain the core 166 in the channel 164 during use.

The second coupling 126, however, is not crimped. Thus, while the crimps at location 168 serve to fixedly couple the first end portion of the core 166 to the adjacent first end section of the body 112 as well as to the first coupling 124, the opposite or second end portion of the core 166 is movable relative to the adjacent, second end section of the body 112 and the second coupling 126. As a consequence, the free portion of the core 166 can move along the channel 164 as needed whenever the force module 110 is bent in an arc or elongated as may occur during opening and closing of the patient's jaws. Such limited movement of the free portion of the core 166 helps insure that the core 166 does not hinder bending or elongation of the force module 110, and yet also facilitates return of the body 112 and the core 166 to their normally straight configuration.

Figure 7:
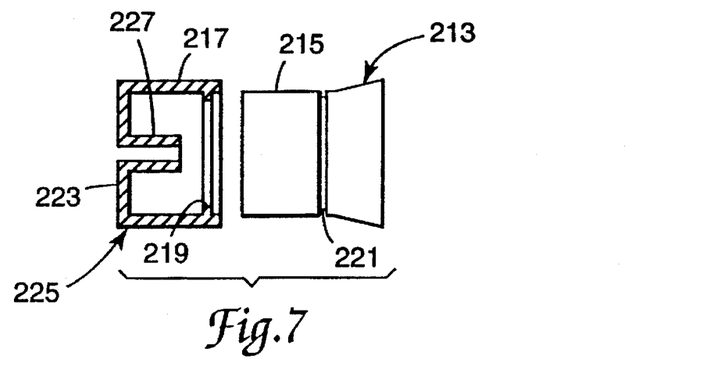
FIG. 7 is an exploded view in partial section of an end portion of a force module according to yet another embodiment of the invention.

FIG. 7 illustrates an alternative construction for one or both ends of the force module (such as the force module 110 shown in FIG. 6). In FIG. 7, a coupling 225 is constructed to non-releasably couple to an end section 215 of a force module elastomeric body 213, although the coupling 225 is illustrated as detached from the end section 215 before assembly.

The coupling 225 includes an outer, generally cylindrical side wall 217. An inwardly extending circular flange 219 extends around and is integrally joined to an inner surface of the side wall 217. When the coupling 225 is joined to the end section 215, the flange 219 snaps into a complementally-shaped groove 221 of the body 213 that circumscribes the end section 215. The end section 215 in this embodiment is cylindrical to match the inner configuration of the side wall 217, although the middle section of the body 213 (not fully shown in FIG. 7) increases in cross-sectional area as the center of the body 213 is approached in a manner similar to the shape of the bodies 12, 112.

The coupling 225 also includes a flat end wall 223 that is integrally connected to the side wall 217. An inner cylindrical sleeve 227 is integrally joined to the end wall 223. The sleeve 227 has an internal cylindrical channel having a diameter that matches the outer diameter of a resilient metallic core of the body 213. The core is not shown in FIG. 7, but is essentially identical to the core 166 illustrated in FIG. 6. The sleeve 227 fits within a cylindrical passage formed in the end section 215 as the body 213 is connected to the coupling 225.

The coupling 225 also includes an arm portion having a hole for connection to an orthodontic appliance. The arm portion is not shown, but is similar to the arm portion 30 illustrated in FIGS. 1–4. The coupling 225 is cast or metal injection molded of stainless steel, or is molded from a high strength thermoplastic such as VECTRA brand liquid crystal polymer. If the coupling 225 is made of a metallic material, the core may be brazed or welded to the sleeve 227. If the coupling 225 is made of a plastic material, the core may be affixed by adhesive (such as epoxy) or heat staked to the sleeve 227.

Those individuals skilled in the art may recognize that a variety of modifications and additions to the presently preferred embodiments are possible without departing from the spirit of our invention. Furthermore, many other orthodontic applications for the force module are possible other than applications correcting a Class II or Class III malocclusion. For example, the force module of the present invention may be used on a single dental arch to move individual teeth as desired. Thus, the invention should not be deemed limited by the embodiments described in detail above, but only by a fair reading of the claims that follow along with their equivalents.

I claim:

1. An orthodontic force module comprising:
a body having a longitudinal axis and made of an elastomeric material, said body having a first end section with a first, outermost end and a second end section with a second, outermost end;
a first coupling connected to said first end section for connecting said first end section to a selected orthodontic appliance in the oral cavity, said first coupling having an arm portion that extends at an obtuse angle relative to said longitudinal axis along a reference axis that intersects said body at a location spaced inwardly from said first end.

2. The force module of claim 1, wherein said force module includes a second coupling connected to said second end section for connecting said second end section to a selected orthodontic appliance in the oral cavity, and wherein said second coupling has an arm portion that extends at an obtuse angle relative to said longitudinal axis along a reference axis that intersects said body at a location spaced inwardly from said second end.

3. The force module of claim 1, wherein said first coupling is movable in an are about said longitudinal axis.

4. The force module of claim 3, wherein said body has a length that remains constant as said first coupling is moved in said arc.

5. The force module of claim 1, wherein said body has a middle section with a certain cross-sectional area in reference planes perpendicular to said longitudinal axis, and wherein said first end section and said second end section each have a cross-sectional area in reference planes perpendicular to said longitudinal axis that is less than said certain cross-sectional area.

6. The force module of claim 1, wherein said first coupling has a through passageway, wherein said body extends through said through passageway and has an enlarged head presenting said first end, said enlarged head located outwardly of said first coupling for retaining said first coupling in connection with said first end section.

7. The force module of claim 6, wherein said body and said through passageway each have a cross-sectional area in directions perpendicular to said longitudinal axis that decreases as said first end is approached.

8. The force module of claim 7, Wherein said first end section and said through passageway each have portions with matching, tapered configurations.

9. The force module of claim 8, wherein said first coupling is movable in an arc about said longitudinal axis.

10. The force module of claim 1 and including a resilient core received at least partially within said body, said core extending in a direction essentially parallel to said longitudinal axis and being made of a material having a greater stiffness than the stiffness of said elastomeric material.

11. The force module of claim 10, wherein said core has a straight configuration.

12. The force module of claim 1, wherein said first coupling is non-integral with said body.

13. The force module of claim 1, wherein said arm portion includes a hole.

14. An orthodontic force module comprising:
a body made made of an elastomeric material said body having a longitudinal axis, a first end section and a second end section; and
a first coupling connected to said first end section and a second coupling connected to said second end section for connecting said first end section and said second end section respectively to selected orthodontic appliances in the oral cavity, wherein said body has a middle section located between said first end section and said second end section, said middle section having a certain cross-sectional area in reference planes perpendicular to said longitudinal axis, and wherein said first end section and said second end section each have a cross-sectional area in reference planes perpendicular to said longitudinal axis that is less than said certain cross-sectional area.

15. The force module of claim 14, wherein said first end section includes a first end and said second end section includes a second end, and wherein said first coupling and said second coupling are spaced inwardly from said first end and said second end respectively.

16. The force module of claim 19, wherein said body is made of an elastomeric material.

17. The force module of claim 14, wherein at least one of said first coupling and said second coupling is movable in an arc about said longitudinal axis, and wherein said force module has an overall length that remains constant as said at least one of said first coupling and said second coupling is moved in said arc.

18. The force module of claim 14 and including a resilient core received at least partially within said body, said core having an elongated, substantially straight configuration extending in a direction essentially parallel to said longitudinal axis, said core being made of a metallic material for enhancing the stiffness of said force module.

19. An orthodontic force module comprising:

a body having a longitudinal axis, said body having a first end section and a second end section;

a first coupling connected to said first end section and a second coupling connected to said second end section for connecting said first end section and said second end section respectively to selected orthodontic appliances in the oral cavity, wherein said body has a middle section located between said first end section and said second end section, said middle section having a certain cross-sectional area in reference planes perpendicular to said longitudinal axis, and wherein said first end section and said second end section each have a cross-sectional area in reference planes perpendicular to said longitudinal axis that is less than said certain cross-sectional area; and a resilient core received at least partially within said body, said core having an elongated, substantially straight configuration extending in a direction essentially parallel to said longitudinal axis, said core being made of a metallic material for enhancing the stiffness of said force module wherein said core has a first end portion fixedly coupled to said first end section of said body and wherein said core has a second end portion that is movable relative to said second end section of said body.

20. The force module of claim 14, wherein said first coupling has a through passageway and wherein said body extends through said passageway and has an enlarged head located outwardly of said first coupling for retaining said first coupling in connection with said first end section.

21. The force module of claim 20, wherein said body and said through passageway each have a cross-sectional area in directions perpendicular to said longitudinal axis that decreases as said head is approached.

22. An orthodontic force module comprising:

a body having a longitudinal axis and made of an elastomeric material, said body having a first end section and a second end section;

a first coupling connected to said first end section and a second coupling connected to said second end section for connecting said first end section and said second end section respectively to selected orthodontic appliances in the oral cavity; and a resilient core received at least partially within said body, said core having an elongated, substantially straight, overall non-helical configuration extending in a direction substantially parallel to said longitudinal axis of said body, said core being made of a metallic material for enhancing the stiffness of said force module.

23. The force module of claim 22, wherein said core has a first end portion fixedly coupled to said first end section of said body, and wherein said core has a second end portion that is movable relative to said second end section of said body.

24. An orthodontic force module comprising:

a body having a longitudinal axis and made of an elastomeric material, said body having a first end section and a second end section;

a first coupling connected to said first end section and a second coupling connected to said second end section for connecting said first end section and said second end section respectively to selected orthodontic appliances in the oral cavity; and a resilient core received at least partially within said body, said core having an elongated, substantially straight configuration extending in a direction substantially parallel to said longitudinal axis of said body, said core being made of a metallic material for enhancing the stiffness of said force module;

wherein said core has a first end portion fixedly coupled to said first end section of said body, wherein said core has a second end portion that is movable relative to said second end section of said body, and wherein said first coupling is crimped to fixedly couple said first end portion of said core to said first end section of said body.

25. An orthodontic force module comprising:

a body having a longitudinal axis and made of an elastomeric material, said body having a first end section and a second end section;

a first coupling connected to said first end section and a second coupling connected to said second end section for connecting said first end section and said second end section respectively to selected orthodontic appliances in the oral cavity; and a resilient core received at least partially within said body, said core having an elongated, substantially straight configuration extending in a direction substantially parallel to said longitudinal axis of said body, said core being made of a metallic material for enhancing the stiffness of said force module;

wherein said core has a first end portion fixedly coupled to said first end section of said body, wherein said core has a second end portion that is movable relative to said second end section of said body, and wherein said first coupling includes a sleeve that is fixedly coupled to said first end portion of said core.

26. The force module of claim 22, wherein at least one of said first coupling and said second coupling is movable in an arc about said longitudinal axis of said body.

27. The force module of claim 26, wherein said force module has an overall length that remains constant as said at least one of said first coupling and said second coupling is moved in said arc.

28. The force module of claim 22, wherein said body has a middle section with a certain cross-sectional area in reference planes perpendicular to said longitudinal axis of said body, and wherein said first end section and said second end section each have a cross-sectional area in reference planes perpendicular to said longitudinal axis of said body that is less than said certain cross-sectional area.

29. An orthodontic force module comprising:

a body having a longitudinal axis and made of an elastomeric material, said body having a first end section and a second end section;

a first coupling connected to said first end section and a second coupling connected to said second end section for connecting said first end section and said second end section respectively to selected orthodontic appliances in the oral cavity; and a resilient core received at least partially within said body, said core having an elongated, substantially straight configuration extending in a direction substantially parallel to said longitudinal axis of said body, said core being made of a metallic material for enhancing the stiffness of said force module.

wherein at least one of said first coupling and said second coupling has a through passageway and wherein said body extends through each through passageway, said body including at least one enlarged head located outwardly of said at least one of said first coupling and said second coupling.

30. The force module of claim 22, wherein said core has a central longitudinal axis and wherein said body has a central longitudinal axis that is collinear with said central longitudinal axis of said core.

31. An orthodontic force module comprising:
- a body having a longitudinal axis and made of an elastomeric material, said body having a first end section with a first, outermost end and a second end section with a second, outermost end;
- a first coupling connected to said first end section for connecting said first end section to a selected orthodontic appliance in the oral cavity, wherein said first coupling has a through passageway, wherein said body extends through said through passageway and has an enlarged head presenting said first end, said enlarged head located outwardly of said first coupling for retaining said first coupling in connection with said first end section.

32. The force module of claim 31, wherein said body and said through passageway each have a cross-sectional area in directions perpendicular to said longitudinal axis that decreases as said first end is approached.

33. The force module of claim 32, wherein said first end section and said through passageway each have portions with matching, tapered configurations.

34. The force module of claim 31, wherein said first coupling is movable in an arc about said longitudinal axis.

35. The force module of claim 34, wherein said body has a length that remains constant as said first coupling is moved in said arc.

36. The force module of claim 31, wherein said body has a middle section with a certain cross-sectional area in reference planes perpendicular to said longitudinal axis, and wherein said first end section and said second end section each have a cross-sectional area in reference planes perpendicular to said longitudinal axis that is less than said certain cross-sectional area.

\* \* \* \* \*

UNITED STATES PATENT AND TRADEMARK OFFICE
CERTIFICATE OF CORRECTION

PATENT NO.: 5,651,672

DATED: July 29, 1997

INVENTOR(S): James D. Cleary and Russell A. Jordan

It is certified that error appears in the above-identified patent and that said Letters Patent is hereby corrected as shown below:

Col. 9, line 62, "are" should read --arc--.

Col. 2, line 35, "are" should read --arc--.

Col. 7, line 46, "fight" should read --right--.

Signed and Sealed this

Twenty-fifth Day of November, 1997

Attest:

BRUCE LEHMAN

Attesting Officer

Commissioner of Patents and Trademarks